US010203282B2

(12) United States Patent
Mente et al.

(10) Patent No.: US 10,203,282 B2
(45) Date of Patent: Feb. 12, 2019

(54) MINERAL WOOL PRODUCT

(71) Applicant: Knauf Insulation, Visé (BE)

(72) Inventors: Markus Mente, Fürnitz (AT); Stefan Kossler, Radenthein (AT)

(73) Assignee: KNAUF INSULATION, Vise (BE)

( * ) Notice: Subject to any disclaimer, the term of this patent is extended or adjusted under 35 U.S.C. 154(b) by 869 days.

(21) Appl. No.: 14/192,065

(22) Filed: Feb. 27, 2014

(65) Prior Publication Data

US 2014/0179009 A1    Jun. 26, 2014

Related U.S. Application Data

(63) Continuation of application No. 13/277,710, filed on Oct. 20, 2011, now abandoned, which is a continuation of application No. PCT/EP2010/055415, filed on Apr. 23, 2010.

(30) Foreign Application Priority Data

Apr. 23, 2009 (DE) .................. 10 2009 018 688

(51) Int. Cl.

| G01N 21/64 | (2006.01) |
| C03C 25/26 | (2018.01) |
| C09K 11/06 | (2006.01) |
| C09K 11/58 | (2006.01) |
| C09K 11/66 | (2006.01) |
| C09K 11/77 | (2006.01) |
| E04B 1/76 | (2006.01) |
| E04B 1/74 | (2006.01) |

(52) U.S. Cl.
CPC ............ *G01N 21/64* (2013.01); *C03C 25/26* (2013.01); *C09K 11/06* (2013.01); *C09K 11/584* (2013.01); *C09K 11/662* (2013.01); *C09K 11/7703* (2013.01); *C09K 11/7761* (2013.01); *C09K 11/7786* (2013.01); *E04B 1/7658* (2013.01); *C09K 2211/1007* (2013.01); *E04B 2001/741* (2013.01); *Y10T 436/13* (2015.01)

(58) Field of Classification Search
CPC ....................... G01N 21/64; G01N 2021/6439
See application file for complete search history.

(56) References Cited

U.S. PATENT DOCUMENTS

| 2,329,959 | A | * | 9/1943 | Van Den Akker | G01N 21/64 |
| | | | | | 250/206 |
| 2,920,202 | A | * | 1/1960 | Motter | C03C 25/246 |
| | | | | | 250/302 |
| 3,778,161 | A | * | 12/1973 | Poulsen | G01J 3/2823 |
| | | | | | 250/486.1 |
| 5,633,077 | A | | 5/1997 | Olinger | |
| 5,736,475 | A | | 4/1998 | Bakhshi et al. | |
| 7,078,359 | B2 | | 7/2006 | Stepanian et al. | |
| 7,666,502 | B2 | | 2/2010 | Magill | |
| 8,044,168 | B2 | | 10/2011 | Gudik-Sorensen | |
| 2002/0097833 | A1 | | 7/2002 | Kaiser et al. | |
| 2003/0087576 | A1 | | 5/2003 | Yang et al. | |
| 2003/0194052 | A1 | | 10/2003 | Price et al. | |
| 2005/0040239 | A1 | | 2/2005 | Durbin | |
| 2005/0083720 | A1 | * | 4/2005 | Fukui | G01N 21/31 |
| | | | | | 365/106 |
| 2006/0205304 | A1 | | 9/2006 | Marzolin et al. | |
| 2008/0003431 | A1 | | 1/2008 | Fellinger et al. | |
| 2008/0003432 | A1 | | 1/2008 | Fellinger | |
| 2008/0020206 | A1 | | 1/2008 | Fay | |
| 2009/0084981 | A1 | * | 4/2009 | Bown | G01N 21/8806 |
| | | | | | 250/459.1 |
| 2009/0181251 | A1 | | 7/2009 | Shooshtari et al. | |
| 2009/0181252 | A1 | | 7/2009 | Shooshtari | |
| 2011/0230111 | A1 | | 9/2011 | Weir et al. | |

FOREIGN PATENT DOCUMENTS

| DE | 29923439 | | 1/2001 |
| DE | 20120904 | U1 | 5/2002 |
| DE | 10237764 | B4 | 7/2006 |
| DE | 19857817 | B4 | 4/2008 |
| EP | 101376 | | 11/1986 |
| EP | 1108694 | | 4/2003 |
| GB | 8148277 | B2 | 4/2012 |
| WO | WO/2010/122133 | A1 | 10/2010 |

OTHER PUBLICATIONS

"Strontianite"; American Heritage Dictionary; 2012.
Davinova, et al., "Fluorescence of alkaline-earth carbonates"; Journal of Materials Science Letters, (1987) 254-256.

* cited by examiner

*Primary Examiner* — Lisa Caputo
*Assistant Examiner* — Alex Devito
(74) *Attorney, Agent, or Firm* — Knauf Insulation; James K. Blodgett

(57) ABSTRACT

The invention relates to a mineral wool product comprising mineral fibers that is marked with an UV or IR active substance and can therefore be identified under exposure to suitable radiation.

23 Claims, No Drawings

MINERAL WOOL PRODUCT

This application is a Continuation of U.S. patent application Ser. No. 13/277,710, filed Oct. 20, 2011, which application is a Continuation of International Application No. PCT/EP2010/055415, filed Apr. 23, 2010, which claims the benefit of German Application No. 102009018688.3, filed Apr. 23, 2009, the entire disclosures of which are hereby incorporated by reference.

This invention relates to a mineral wool product comprising mineral fibers, particularly mineral wool adapted for use as a building material in buildings and/or civil engineering, particularly as thermal and/or acoustic insulation, and more particularly to such a product whose provenance may be easily traced.

The term mineral fiber is intended to include stone wool fibers, glass wool fibers, slag fibers, and ceramic fibers.

Mineral wool products are used in various forms and applications including:

Forms:
 loose, untreated mineral wool (for example, blowing wool)
 loose mineral wool with uncured binding agent (for example, blowing wool)
 needled mineral wool products without a binding agent, but comprising a lubricant (e.g. a lubricating oil)
 mineral wool mats, mineral wool panels and mineral wool moulded parts, provided with a cured or uncured binding agent
 composite bodies with a mineral wool layer, for example composite panels with a layer of bonded wood wool and a layer of mineral wool comprising a cured binding agent Applications:
 thermal and/or acoustic insulation in buildings and civil engineering
 thermal and/or acoustic insulation of: electrical appliances such as refrigerators; cars; industrial installations and their parts
 growth base for plants Typical properties for such mineral wool products may include:
 the mineral fibers being short (rather than being continuous, long fibers) and thin (average diameter generally <10 µm)
 such products made from mineral fibers have high open porosity, generally >70% by volume
 the amount of binding agent or lubricant agent proportion (if present) is usually between 0% and 12% by weight with respect to the mineral wool product
 the binding agent (if present) may comprise phenol formaldehyde or a binding agent that is free from phenol formaldehyde In accordance with the invention, the amount of the binding agent or lubricant (if present) may be, for example, between 0.01 and 10% by weight or between 0.1 and 8% by weight with respect to the mineral wool product. In accordance with one specific example, the amount of binding agent or lubricant is between 0.2 and 5% by weight.

The binding agent may be used to provide markings to the mineral wool products. To do this, the binding agent may be purposefully discolored, for example with hot air, electrical heaters or laser beams (EP 1 108 694 B1; DE 3 229 601 A1; DE 29 822 362 U1).

One aspect of the invention is based on providing mineral wool products with a marking in a non-destructive way, particularly without requiring any particular precautions during manufacturing. A further aspect of the invention is based upon providing mineral wool products with a marking which does not detract from the appearance of the product and/or can be easily detected or revealed, particularly when the product has been installed.

The invention is based on the knowledge that these objectives can be achieved in a completely different way, i.e. by applying components to the mineral wool product that do not detrimentally physically change the mineral wool product as such, and are neither optically nor physically visible, but become visible when ultra-violet (UV) or infra-red (IR) radiation is directed at them.

UV radiation is invisible to humans and has a wavelength of approximately 10 to 400 nm, while IR radiation covers the wavelength range of greater than 780 nm up to approximately 1300 nm.

The specified components are UV or IR active substances in which the coloring can only be seen with the naked eye under ambient conditions when irradiated with a source of UV or IR radiation. Hence, for example, a UV light source stimulates the UV active substances in the mineral wool product to produce a visible fluorescence. The specified components form a type of optical converter, which for example, converts incident UV radiation of a specific wavelength into visible light with a longer wavelength.

Generally, the wavelength of the emitted light is greater than that of the stimulating light. For IR radiation with wavelengths >780 nm, this generally means that direct conversion in to visible light with wavelengths between 400 and 780 nm is not possible.

Some crystalline luminescent materials are visibly fluorescent if they are stimulated with blue or ultraviolet light. Through a specific crystal doping, however, it is possible to suppress such spontaneous emission, and the stimulating energy then remains stored. IR radiation then releases the stored energy, allowing emissions in the range of visible light. Under the influence of IR radiation, the IR active components, or alternatively the respective zones/areas with IR active components, illuminate. Corresponding IR active components can be used as such or they may be already charged (pre-stored). In the first case, they must be charged with UV radiation (activated) before their actual use.

Mineral wool product according to preferred embodiments of the invention can not be identified as such (from the outside) or be differentiated from a conventional mineral wool product under normal, ambient conditions, that is to say that the marking remains "invisible" under normal conditions. This may be important for optical reasons, for example for mineral wool elements that are used in interior finishing with visible surfaces.

The latently effective colorants (UV or IR active substances), however, make it possible to identify the product at any time if need be, notably by subjecting the product to a level of incident UV or IR radiation which reveals the marking. It is even possible to charge the IR indicators by means of UV radiation, for example, only when their presence is to be checked.

This results in the following important advantages over mineral wool products with known types of marking of the type previously specified:
 the binding agent or the lubricant remain completely effective
 the physical properties of the product remain unchanged or substantially unchanged
 the optical properties or visual appearance of the product can be chosen freely independent of any possible marking In one of its aspects, the invention relates to a mineral wool product that comprises at least one UV or IR active component and, optionally, a binding agent (which may be formaldehyde-based or formaldehyde-free).

When present, any suitable binder may be used including formaldehyde containing binders (for example phenol formaldehyde binders) and binders which are formaldehyde free. The term "formaldehyde free" in relation to binders is intended to indicate that the constituents making up the binder do not comprise formaldehyde, particularly free formaldehyde, and\or do not release formaldehyde in ordinary usage. Examples of binding agents that do not contain formaldehyde are binding agents that are obtained from an amine component and a sugar, particularly a reducing sugar, which may comprise melanoidins or glycosylamines. Specific examples of formaldehyde-free binding agents that can be used according to the invention are described in WO 2007/014236. These specific examples include binders based on a sugar, particularly a reducing sugar (for example dextrose), an acid or an acid precursor (for example triammonium citrate) and a source of nitrogen.

The UV or IR active component may be distributed through the mineral fiber product for example homogenously amongst the mineral fibers. For example, the coloring component can be admixed to a carrier medium, for example a binder and added to the fiber flow in the conventional way when manufacturing the mineral wool product and thereby distributed homogenously through the product. Alternatively, the UV or IR active component may be added to a dispersion medium or a suitable solvent or sprayed onto the mineral wool product in a pure form. The UV or IR active component is preferably applied to the mineral fibers before curing of any binder of the mineral fiber product.

The UV or IR active component may include other substances such as, for example, ethidiumbromide, amino acids like tryptophan, tyrosine, and phenylalanine, or peptides and proteins.

The at least one UV or IR active component (also called an indicator substance) may be applied separately to a so-called fiber cloud (e.g. immediately after manufacture of fibers from a melt), or applied separately to an already manufactured primary fleece or secondary fleece, for example spayed on. In like manner, the UV or IR active substance can also be applied to a finished fiber product, especially if a specific area on the surface of the product is to be marked.

If the indicator substance is distributed throughout the mineral fiber product, for example via a homogenous distribution of the indicator substance in the product, this may be seen under UV or alternatively IR light as an essentially uniform color, for example a green or red color.

The indicator substance may allow products from different plants or different years of production to be readily identified, for example by using a particular indicator substance as an indication of year of manufacture and/or site of manufacture.

This type of marking/identification can, of course, also be achieved with only partial distribution of the indicator substance. With targeted, partial application, for example on a section of the surface, it is possible to form appropriately colored zones of any shape as a marking. For example, company names, product names, trademarks, pictures, standards, manufacturing data, product characteristics, etc. can be shown specifically. The locally applied UV and IR active components for such markings, applied on a surface area, may be coated or sprayed on, for example, or applied as a suspension by means of stamps.

When the marking/identification is applied only to a section of the surface of a product, subsequent examination of that particular surface is required to determine the presence or absence of the marking/identification. One advantage of distributing the indicator substance throughout the mineral fiber product is that examination of any portion of the mineral fiber product may be used to reveal the presence or absence of the marking/identification. For example, where the mineral wool product is installed in a cavity wall, any easily accessible portion of the mineral wool product may be examined in situ (without dismantling the wall to reveal an entire surface of the mineral wool product) or a sample of the mineral wool product may be removed for examination. Similarly, distribution of the indicator substance throughout the mineral fiber product is particularly advantageous where it not feasible to apply a marking/identification to a surface of the mineral wool product, for example for blowing wool.

The at least one UV active component may comprise at least one compound from the group consisting of: flavonic acid, 4,4' Distyryl-biphenyls, stilbenes, pyrazolines, coumarin, dihydroquinolines, naphthalene acid imides, benzoaxazole, benzioxazole compounds, riboflavin, quinine, chlorogenic acid, quinoline yellow, and derivatives thereof.

The indicator substance may be used as a powder or in a liquid preparation, for example in aqueous solution or as a viscous liquid.

The at least one IR active component may comprise a compound selected from the group consisting of doped (not radioactive) strontium sulphide, doped zinc sulphide, yttrium compounds, ytterbium compounds and erbium compounds. The strontium sulphide may be doped with europium and/or samarium; the zinc sulphide may be doped with copper and/or lead.

For example, areas that contain yttrium-ytterbium-erbium compounds appear green under IR radiation.

Many IR active components can also be used as UV active substances because they have their own UV fluorescence.

The percentage by weight of the UV or IR active component, based on the total mineral wool product or alternatively the mineral wool component (for composite structural elements), may be less than 1.0% by weight. For example, the percentage by weight of the UV or IR active component based on the entire mineral wool product or alternatively the mineral wool proportion may be less than 0.5% by weight or less than 0.2% by weight.

If one relates the proportion of the UV or IR active component to the mass of the binding agent or lubricant, then the amount is usually from 0.1% to 5% by weight. The proportion of the UV or IR active component based on the mass of binding agent or lubricant may be 0.2% to 3% by weight or 0.2% to 1.5% by weight.

Water soluble UV or IR active components have the advantage that they are easy to apply in a liquid or viscous preparation, for example they may be sprayed on or injected.

The mineral wool product may be provided with one or more of the specified coloring components, for example in order to make one or more colors recognisable under the respective light. For some applications it is sufficient to use the light active components only in specific sections of the product, for example on one surface or in an area that is close to the surface. Due to the high open porosity of the fiber products, it is also possible to color identify zones that are below the surface.

Preferred or alternative characteristics are defined in the dependent claims. The following examples, from which characteristics may be used individually or in any combination in relation to the invention, should not be considered as limiting.

EXAMPLE 1

Stone wool fibers are spun from a stream of mineral fiber melt using a series of external spinning wheels. In the flow of fibers created as the fibers leave the spinning wheels and are carried in a forced air stream towards a collecting apparatus, a mixture of phenol formaldehyde binder (3% by weight based on the finished product) and stilbene (0.3% by weight based on the finished product) is injected (sprayed) homogeneously. A primary fleece is then formed from the collected fibers in the usual way and a secondary fleece is then formed by folding the primary fleece, ultimately resulting, once passed through an oven to cure the phenol formaldehyde binding agent, in a mineral wool matt with a density of 40 kg/m$^3$ adapted for insulating between rafters.

Even at the end of the life of the product, for example 50 years later, for example when demolishing a house insulated using the product, it is possible by means of UV irradiation to color activate the stilbene component and, based on the coloring, to identify for example the year of manufacture and/or the manufacturer and/or the manufacturer's plant.

EXAMPLE 2

A mixture of binding agent (for example a phenol formaldehyde binder) and zinc sulphide doped with copper and lead, is applied to one surface of a conventionally manufactured finished mineral fiber panel having a density of 150 kg/m$^3$. This is carried out by spraying the indicator substance while using a mask to apply an identifier in the form of a barcode on the surface. The barcode may contain information such as the manufacturer, type of product, product properties, year of production, etc. The area where the identifier is applied is subsequently charged by means of UV radiation. The identifier is optically invisible to the naked eye under normal ambient lighting conditions, but can be rendered visible at any time under IR radiation.

What is claimed is:

1. A method of identifying a mineral wool insulation product comprising mineral fibers comprising:
providing the mineral wool insulation product with a marking provided by an active indicator substance which is configured to emit visible light by a method consisting of irradiating the active indicator with UV or IR radiation, wherein the indicator substance is present in an amount that is less than 1% by weight based on the total weight of the mineral wool insulation product, wherein the active indicator substance is selected from the group consisting of UV indicator substances that are visible to the naked eye under a source of UV radiation and IR indicator substances that are visible to the naked eye under a source of IR radiation, and wherein the marking is invisible under normal ambient conditions;
subjecting the product to a level of incident UV or IR radiation which reveals the marking; and
identifying with the naked eye the mineral wool insulation product on the basis of the revealed marking.

2. The method of claim 1, wherein the active indicator substance is distributed homogeneously through the mineral wool product.

3. The method of claim 1, wherein the marking is arranged in at least one locally limited section.

4. The method of claim 1, wherein the marking is arranged at at least one section of a surface of the product.

5. The method of claim 1, wherein the marking is selected from the group consisting of a company name, a product name, a trademark, a picture, a standard, manufacturing data and product characteristics.

6. The method of claim 1, wherein the marking provides an indication selected from an indication of the year of manufacture and the site of manufacture of the mineral wool insulation product.

7. The method of claim 1, wherein the active indicator substance is present with a carrier medium in a mixture.

8. The method of claim 1, wherein the active indicator substance is present with a binding agent or a lubricant in a mixture.

9. The method of claim 1, wherein the active indicator substance comprises at least one UV indicator substance selected from the group consisting of flavonic acid, 4,4'-distyryl-biphenyls, stilbenes, pyrazolines, coumarin, dihydroquinolines, naphthalene acid imides, benzoaxazole, benzioxazole compounds, riboflavin, quinine, chlorogenic acid, quinoline yellow, and derivatives thereof.

10. The method of claim 1, wherein the active indicator substance comprises at least one IR indicator substance selected from the group consisting of doped strontium sulfide, doped zinc sulfide, yttrium compounds, ytterbium compounds and erbium compounds.

11. The method of claim 1, wherein the active indicator substance is water soluble.

12. The method of claim 1, wherein the active indicator substance is monochromatically fluorescent.

13. The method of claim 1, wherein the mineral wool product is blowing wool.

14. The method of claim 1, wherein the amount of active indicator substance in the mineral wool insulation product is less than 0.5% by weight based on the total weight of the mineral wool insulation product.

15. The method of claim 1, wherein the amount of active indicator substance in the mineral wool insulation product is less than 0.2% by weight based on the total weight of the mineral wool insulation product.

16. The method of claim 1, wherein the active indicator substance is present with a binding agent and the amount of indicator substance in the binding agent is from 0.1% to 5% by weight.

17. The method of claim 1, wherein the active indicator substance is present with a lubricant and the amount of the indicator substance in the lubricant is from 0.1% to 5% by weight.

18. A method of identifying a mineral wool insulation product comprising mineral fibers comprising:
providing the mineral wool insulation product with a marking provided by an active indicator substance configured to be visible under the naked eye by a method consisting of subjecting the active indicator substance to a source of UV radiation, wherein the active indicator substance comprises a UV indicator substance which converts incident UV radiation of a specific wavelength in to visible light with a longer wavelength and which is visible to the naked eye under a source of UV radiation;
subjecting the product to a level of incident UV radiation which reveals the marking; and
identifying with the naked eye the mineral wool insulation product on the basis of the revealed marking.

19. The method of claim 18, wherein the indicator substance is present in an amount that is less than 1% by weight based on the total weight of the mineral wool insulation product.

20. The method of claim 18, wherein the marking is invisible under normal ambient conditions and is revealed by subjecting the product to a level of incident UV radiation which reveals the marking.

21. The method of claim 18, wherein the active indicator substance is selected from the group consisting of flavonic acid, 4,4'-distyryl-biphenyls, stilbenes, pyrazolines, coumarin, dihydroquinolines, naphthalene acid imides, benzoaxazole, benzioxazole compounds, riboflavin, quinine, chlorogenic acid, quinoline yellow, and derivatives thereof.

22. A method of identifying a mineral wool insulation product comprising mineral fibres comprising:
   providing the mineral wool insulation product with a marking provided by an active indicator substance which emits visible light by a method consisting of irradiating with UV or IR radiation, wherein the indicator substance is present in an amount that is less than 1% by weight based on the total weight of the mineral wool insulation product, wherein the active indicator substance is selected from the group consisting of:
   a) UV indicator substances that are visible to the naked eye under a source of UV radiation and selected from the group consisting of flavonic acid, 4,4'-distyryl-biphenyls, stilbenes, pyrazolines, coumarin, dihydroquinolines, naphthalene acid imides, benzoaxazole, benzioxazole compounds, riboflavin, quinine, chlorogenic acid, quinoline yellow, and derivatives thereof; and
   b) IR indicator substances that are visible to the naked eye under a source of IR radiation and selected from the group consisting of doped strontium sulfide, doped zinc sulphide, yttrium compounds, ytterbium compounds and erbium compounds; and
   wherein the marking is invisible under normal ambient conditions;
      subjecting the product to a level of incident UV or IR radiation which reveals the marking; and
      identifying with the naked eye the mineral wool insulation product on the basis of the revealed marking.

23. The method of claim 22, wherein the active indicator substance is an UV indicator substance.

\* \* \* \* \*